United States Patent [19]
Gurmarnik et al.

[11] Patent Number: 5,306,239
[45] Date of Patent: Apr. 26, 1994

[54] METHOD OF AND SET FOR SPINAL ANESTHESIA

[76] Inventors: Simon Gurmarnik, 38 Garrison Rd., Brooklyne, Mass. 02146; Konstantin Kandror, 314 Langley Rd., Newton, Mass. 02159

[21] Appl. No.: 99,524

[22] Filed: Jul. 30, 1993

[51] Int. Cl.⁵ .............................. A61M 31/00
[52] U.S. Cl. ......................... 604/51; 604/158; 604/164; 604/264; 604/273
[58] Field of Search .......... 604/51, 158, 164, 264, 604/272, 273; 206/570, 571

[56] References Cited

U.S. PATENT DOCUMENTS

| | | | |
|---|---|---|---|
| 4,128,173 | 12/1978 | Lazarus et al. | 206/570 |
| 4,917,670 | 4/1990 | Hurley et al. | 604/51 |
| 4,994,036 | 2/1991 | Biscoping et al. | 604/164 |
| 5,085,631 | 2/1992 | Leighton | 604/158 |
| 5,106,376 | 4/1992 | Mononen et al. | 604/158 |
| 5,160,323 | 11/1992 | Andrew | 604/158 |
| 5,209,734 | 5/1993 | Hurley et al. | 604/158 |
| 5,232,442 | 8/1993 | Johnson et al. | 604/158 |

Primary Examiner—C. Fred Rosenbaum
Assistant Examiner—N. Kent Gring
Attorney, Agent, or Firm—I. Zborovsky

[57] ABSTRACT

A spinal anaesthesia is performed with the use of a step and instruments for removing an antiseptic substance after its application of patient's skin for disinfection and before introduction of a spinal needle, to prevent contamination of central nervous system by the anticeptic substance which otherwise would be introduced with the needle tip.

3 Claims, 2 Drawing Sheets

METHOD OF AND SET FOR SPINAL ANESTHESIA

BACKGROUND OF THE INVENTION

The present invention relates to a method of and a set for spinal anesthesia.

Spinal anesthesia is well known in medical practice. As shown in FIG. 1, a spinal needle 2' with a stylet 1' is introduced via an introducer 3' through a skin 4', ligamentum flavum 5', epidural space 6', dura mater 7, arachnoid 8' into a subarachnoid space 9' with spinal fluid, where peripheral nerves emerge from the spinal cord and a small amount of local anesthetic introduced through the needle into the space 9' causes a profound anesthesia from the waist down. A major problem with the spinal anesthesia is a PDHP causing headaches and contributed to a loss of spinal fluid through a hole made by the spinal needle. From more than 2 million of diagnostic spinal punctures the incidents of PDPH constitute up to 8% despite the ever reducing diameter of the needles.

In 1989 we suggested (ANAESTHESIA, UK and Ireland, v.20:4:14,1989) that a small amount of antiseptic solution used for skin preparation reaches the subarachnoid space with the tip of the needle bypassing the brain barrier, it contaminates the central nervous system of the patient with highly toxic antiseptic solution and causes the development of benign aseptic self-limited meningismus (PDHP). It was proposed as a hypothesis to wash off the antiseptic solution before administration of anaesthesia by the spinal needle. The prevention of PDHP has been achieved by us in 1086 cases over the last 5 years in our experiments, in which we removed the antiseptic from the patient prior to the administration of anaesthesia.

In known methods of spinal anaesthesia no steps of removal of antiseptic solution were proposed. In known sets for spinal anaesthesia no means were provided for the antiseptic solution removal, as can be seen from FIG. 2 in which the set support S has only an antiseptic application section 2 provided with antiseptic application grip sponges 1, and a spinal anaesthesia section 7 provided with syringes, spinal needle, stylet, introducer, anaesthesia solution reservoir, etc.

SUMMARY OF THE INVENTION

Accordingly, it is an object of the present invention to provide a method of and a set for spinal anaesthesia, in accordance with which PDPH is reliable preventing.

In keeping with these objects and with others which will become apparent hereinafter, one feature of the present invention resides, briefly stated, in a method of and a set for spinal anaesthesia, in which a step and a means are provided correspondingly, for removing an antiseptic substance applied on the patient's skin, immediately before the administration of an anaesthetic substance to a patient by a spinal needle.

When the method is performed and a set is designed in accordance with the present invention, no antiseptic substance is introduced with the tip of the spinal needle into the subarachnoid space, no contamination takes place, and no PDPH occurs.

The novel features of the present invention are set forth in particular in the appended claims. The invention itself both as to its construction and its manner of operation will be best understood from the following description of preferred embodiments, which is accompanied by the following drawings.

DESCRIPTION OF PREFERRED EMBODIMENTS

Figure 1:
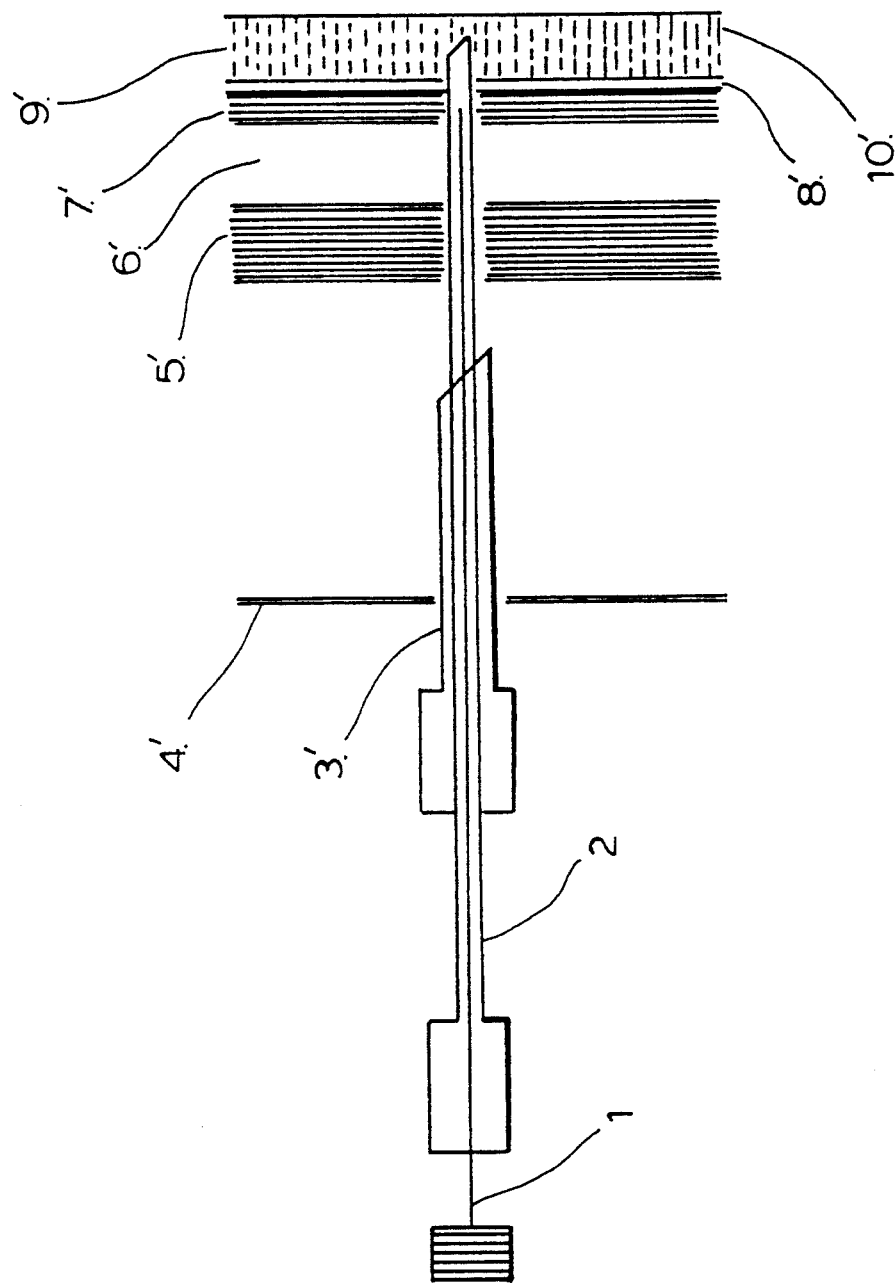
FIG. 1 is a view schematically showing the procedure of administering of spinal anaesthesia.
Figure 2:
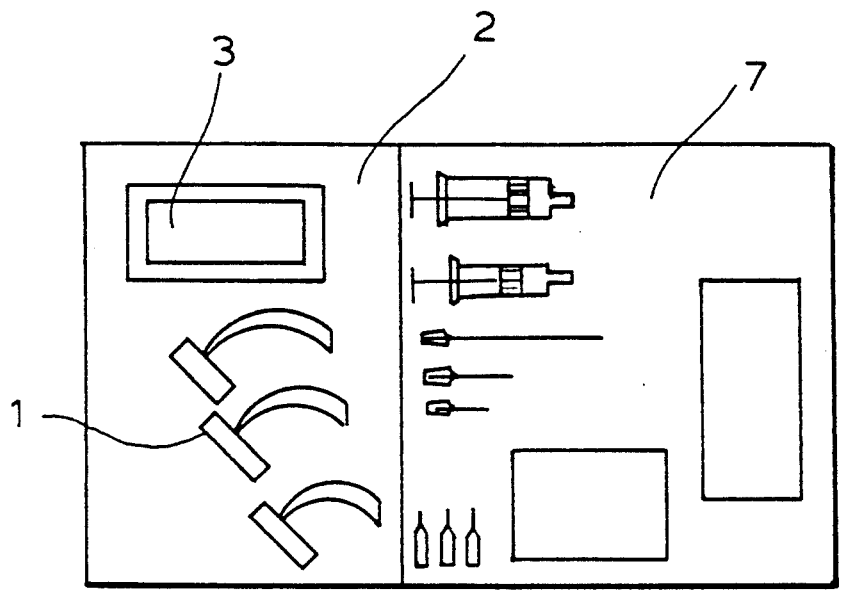
FIG. 2 is a view showing a set for spinal anaesthesia in accordance with the prior art.
Figure 3:
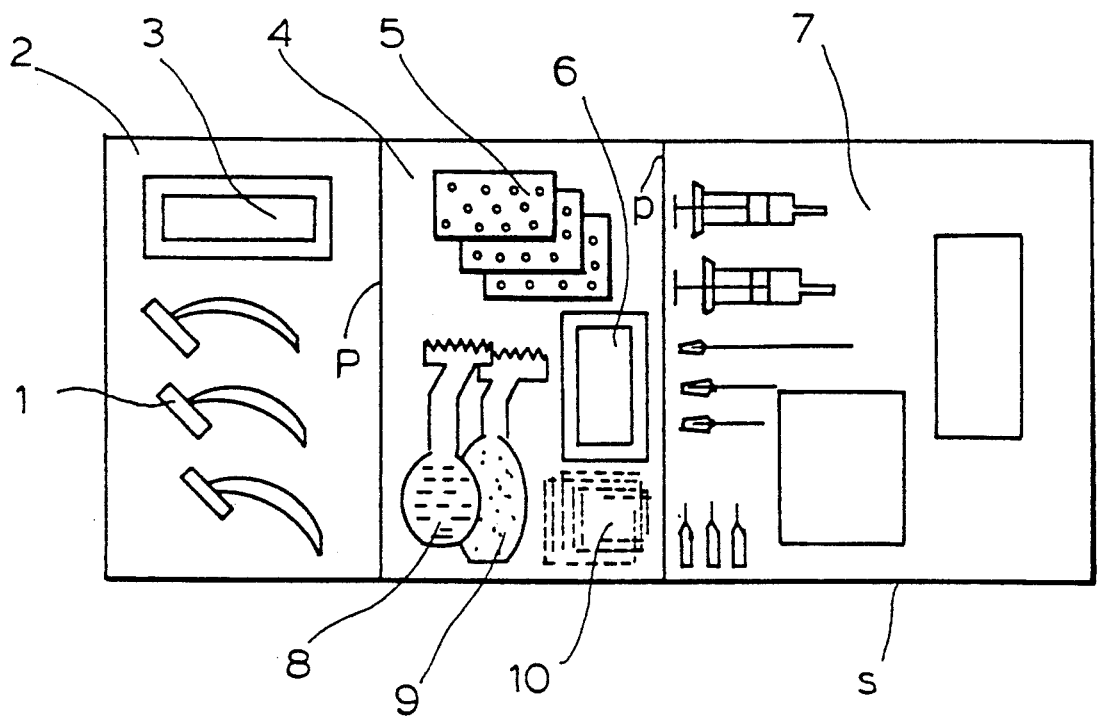
FIG. 3 is a view showing a set for spinal anaesthesia in accordance with the present invention.

As can be seen from FIG. 3, a set for spinal anaesthesia in accordance with the present invention has a support S which has an antiseptic application section 2, an antiseptic removal section 4 and a spinal anaesthesia section 7. The sections can be separated from one another by painted lines or upstanding partitions P. The sections are located one after the other in the longitudinal direction of the support S in the order listed above. This order corresponds to the order in which respective elements accommodated in the sections are to be used.

The antiseptic application section 2 of the support S supports antiseptic application grip sponges 1 and an antiseptic solution reservoir 3. The antiseptic removal section 4 of the support S supports absorbent towels 5, a water reservoir 6, water pre-filled, big cellulose grip sponges 8 and 9, and dry fabric sponges 10. The apinal anaesthesia section 7 of the support S supports syringes, spinal needle, introducer, stylet, anaesthetic solution reservoir, etc. All elements can be retained by known flexible clamps.

During the process of anaesthesia an antiseptic substance such as Povidon-iodine (Betadine) is used to disinfect a skin area by applying it from the reservoir 3 with soft synthetic small sponges 1 for example of polyurethane. The scrub begins at the scope of proposed insertion of the needle and proceeds to the periphery of the area. The entire procedure is repeated prior to the spinal tab. Then in accordance with the present invention, the antiseptic substance is removed. For this purpose since skin is porous absorbable formation, the involved area on which the antiseptic substance has been applied, is gently soaked and than rinsed with water by water prefilled grip sponges 8, 9 because Povidone is water-soluble. Then washing off is performed with water from the reservoir 6, and the area is finally soaked off by the absorbent towel 5. The entire procedure should be repeated again. After this, the spinal needle penetrates the skin which is antiseptic free and dry. Therefore, the probability of unintentional Povidone contamination of the central nervous system is minimized, so as to totally eliminate the problem of PDPH.

The present invention is not limited to the details shown since various modifications and structural changes are possible without departing in any way from the spirit of the invention.

What is desired to be protected by Letters Patent is set forth in the appended claims.

We claim:

1. A method of spinal anesthesia, comprising the steps of
    applying an antiseptic substance on an area of patient's skin;
    administering an anesthetic substance into a spinal space by a spinal needle penetrating through said area of patient's skin;

withdrawing the spinal needle from patient after said administering; and immediately before said administering, removing the antiseptic substance from the area of patient's skin to prevent penetration of the antiseptic substance through the patient's skin during said administering.

2. A method as defined in claim 1, wherein said removing includes soaking the area of patients skin with a removing substance, rinsing the area with water, washing off the removing substance with water, and soaking up with an absorbent article.

3. A method as defined in claim 2, wherein said soaking, rinsing, washing off and soaking up is repeated several times before said administering step and during said removing step .one after another.

* * * * *